United States Patent [19]
Kligerman et al.

[11] Patent Number: 5,972,321
[45] Date of Patent: Oct. 26, 1999

[54] ACID NEUTRALIZATION OF SKIN

[75] Inventors: Alan E. Kligerman, Egg Harbor Township; Sarah Rogers, Mays Landing, both of N.J.

[73] Assignee: AkPharma Inc., Pleasantville, N.J.

[21] Appl. No.: 09/107,359

[22] Filed: Jun. 30, 1998

[51] Int. Cl.[6] .............................. A61K 7/32; A61K 7/34; A61K 7/36; A61K 7/38; A61K 7/00
[52] U.S. Cl. ............................... 424/65; 424/66; 424/67; 424/68; 424/400; 424/401
[58] Field of Search .................................. 424/65, 66, 67, 424/68, 400, 401

[56] References Cited

U.S. PATENT DOCUMENTS

| | | | |
|---|---|---|---|
| 5,672,351 | 9/1997 | Chikindas et al. | 424/401 |
| 5,817,351 | 10/1998 | De Wille et al. | 426/74 |
| 5,869,119 | 2/1999 | Kligerman et al. | 426/74 |

*Primary Examiner*—Shelley A. Dodson
*Attorney, Agent, or Firm*—Panitch Schwarze Jacobs & Nabel, P.C.

[57] ABSTRACT

Methods and compositions using calcium glycerophosphate for the deacidification of the skin and treatment of dermatological conditions, including body odor and dermatological discomfort, are provided. Body odors, such as odor associated with axillary, foot, facial, scalp, and anal-genital regions, may be treated by the application of calcium glycerophosphate to the affected area or to the materials in contact with the affected area. Dermatological discomfort, such as dermatological discomfort associated with acidic body fluids or with the application of cosmetics or therapeutic formulations, may also be treated by the application of calcium glycerophosphate. The calcium glycerophosphate may be used alone in powdered form, or in a liquid, solid or semi-solid vehicle, with or without the addition of other active ingredients and/or excipients.

5 Claims, No Drawings

ACID NEUTRALIZATION OF SKIN

BACKGROUND OF THE INVENTION

The invention relates to methods and products for neutralizing acid on dermatological surfaces of animals, particularly humans.

In human skin, sebaceous glands, eccrine sweat glands and apocrine glands secrete various chemicals onto the skin surface. These chemicals include sodium chloride, potassium bicarbonate, lactic acid, urea, squalene, proteins, carbohydrates, triglycerides and other lipids. Although body odor may be partially due to certain chemicals secreted by sebaceous glands and eccrine sweat glands, major axillary (underarm) foul odor is due to secretions of the apocrine glands, which contain special nutrient materials for microorganisms.

Apocrine glands are located primarily in the axillae, anal-genital region, mammary areolae, ear canals, eyelids, and are scattered on parts of the face, anterior chest and abdomen. In general, the apocrine duct opens into the upper end of the hair follicle, although the duct occasionally opens directly onto the skin surface. In contrast to the eccrine glands, which produce a clear watery liquid, the apocrine glands secrete a milky fluid that has a pH range of 5 to 6.5 and initially consists of lipids, proteins and carbohydrates. Although fresh apocrine secretions do not have an objectionable odor, the secreted compounds are found to undergo decomposition by both chemical and microbial actions, and the degradation products are responsible for the offensive odors. Chemical substances identified as contributing to this unpleasant odor include lower organic acids such as butanoic, isopentanoic, hexanoic and octanoic acids; mercaptans; indoles; amines; hydrogen sulfide; ammonia; and phosphine. Although gram-positive bacteria, which thrive on substances found on the moist skin surface, appear to be responsible for the production of malodor, the precise mechanisms of odor production are still unclear.

Most deodorant or antiperspirant products on the market today are salts of aluminum, zirconium and/or zinc. The aluminum salts include aluminum chloride, aluminum chlorhydroxide, aluminum sulfate, aluminum potassium sulfate and aluminum phenolsulfonate; the zirconium salts include particularly zirconium oxychlorides and hydroxychlorides; and the zinc salts comprise zinc oxide, zinc peroxide, zinc stearate and zinc phenolsulfonate.

Although long-term use of aluminum, zirconium and/or zinc salts as underarm deodorants presents no major problems in toxicity, these compounds frequently cause irritation, burning, itching or other uncomfortable sensations to individuals with sensitive skin. These individuals may stop using commonly available underarm deodorants because of persistent itching or burning after use. Moreover, such irritation, burning and itching caused by underarm deodorants makes them even less suitable for application to other areas of the body which are even more sensitive than the underarm. Development of other efficacious anti-odorant substances which do not cause irritation or uncomfortable sensation when applied to the skin is therefore desirable.

BRIEF SUMMARY OF THE INVENTION

The invention relates to compositions and methods for deacidification of animal skin, particularly human skin. The invention further relates to a method of treating body odor in a human comprising the application of calcium glycerophosphate to a body odor affected area, including but not limited to the underarm area and the foot area.

The invention also relates to a method of treating dermatological discomfort in a human comprising the application of calcium glycerophosphate to an affected area.

DETAILED DESCRIPTION OF THE INVENTION

According to the present invention, it has been found that certain dermatological conditions including body odor and dermatological discomfort may be treated by the topical application of calcium glycerophosphate (CGP). Therefore, the present invention entails methods of treatment of dermatological conditions by the topical application of CGP, alone or in various compositions or formulations. The present invention also entails CGP formulations which are particularly suitable for treatment of dermatological conditions by topical application.

Without wishing to be limited by any particular theory, it is believed that the topical application of CGP exerts a salutary effect on dermatological skin conditions by increasing the pH in the areas of application. Topical application of CGP may inhibit the growth of acidophilic bacteria which contribute to body odor, thereby mitigating body odor. Additionally, topical application of CGP may neutralize acid body substances which can be a source of irritation, particularly in sensitive body areas.

"Treatment", as used herein, refers to any topical application of CGP for the purposes of preventing or ameliorating any dermatological condition. Dermatological conditions which may be treated with CGP according to this invention, include but are not limited to body odor and dermatological discomfort.

Body odor may be treated by the application of a CGP formulation to a body odor affected area. A "body odor affected area", as used herein, refers to any area of the skin which has odor associated with it, including but not limited to the armpit, scalp, foot, face, and anal-genital areas.

CGP may be applied directly to the body odor affected area or to a material which is maintained in close contact with the body odor affected area. For example, underarm body odor may be treated by applying CGP to the underarm. As another example, foot odor may be treated by applying CGP directly to the toes or sole of the foot or to footwear such as shoes or stockings.

Dermatological discomfort which may treated by the application of CGP to the affected area according to the present invention includes discomfort that results from the secretion or excretion of body substances and discomfort that results from the application of acidic substances. Dermatological discomfort includes, but is not limited to wetness and skin irritation, such as burning or itching. Dermatological discomfort may be treated by the application of CGP directly to the affected area or indirectly by application of CGP to a material that is maintained in close contact with the affected area.

The acid of normal body substances can be a source of dermatological discomfort. These body substances include urine, for both infants and adults, and acid perspiration. Additionally, bowel movements may be acidic, especially in infants. Acidic bodily substances may be especially irritating on sensitive skin areas, including but not limited to pimples, cuts, inflamed tissue areas, and anal-genital tissues.

More specifically, CGP may be applied to treat diaper rash. CGP may be applied to the affected areas of the infant. Advantageously, the CGP may be in the form of a dusting powder that is applied to the diaper or that is manufactured as a component of the diaper. Because CGP can be consumed as food and is not injurious to eyes or lungs, it is eminently suitable as a product for use with infants. CGP may also be used in conjunction with adult diapers in the same manner as it is used with infant diapers.

Other non-limiting examples where CGP may be used to treat dermatological discomfort include hospital and nursing home settings where patient skin irritation results from spending long periods of time in a sitting or reclining position. Such dermatological discomfort may be treated by application of a CGP formulation to the affected area. Additionally, CGP may be used in personal grooming facilities including but not limited to barbershops, hair salons, tanning salons, and massage salons to prevent or ameliorate dermatological discomfort that results from procedures or products used therein.

A dermatological condition that may also be treated with application of CGP is dermatological discomfort that results from the application of acidic substances to the skin. For example, the active ingredients of certain cosmetic or therapeutic (medicinal) products are acidic in nature and may cause discomfort or irritation when applied to the skin. CGP may be incorporated into the cosmetic product to neutralize the acidity of the cosmetic product, or CGP may be applied before or after application of the therapeutic or cosmetic product to mitigate discomfort that results from application of the therapeutic or cosmetic product. Examples of cosmetic products that may be used in conjunction with CGP application include but are not limited to makeup products, perfumes, tanning agents, depilatory agents, sunscreen and sunblock agents, anti-aging and anti-wrinkle agents, skin lightening agents, and depigmenting agents. Examples of therapeutic products that may be used in conjunction with CGP include local analgesics and anesthetics, anti-acne agents, anti-bacterial agents, anti-yeast agents, anti-fungal agents, anti-viral agents, anti-dermatitis agents, anti-pruritic agents, anti-inflammatory agents, anti-psoriatic agents, vitamins, corticosteroids, hormones and retinoids.

Calcium glycerophosphate (CGP) is also known as 1,2,3-propanetriol, mono(dihydrogen phosphate) calcium salt (1:1), calcium glycerinophosphate, calcium phosphoglycerate and Neurosin®. It has a molecular formula of $C_3H_7CaO_6P$ and a formula weight of 210.14 (anhydrous). It may exist as a hydrate, including the monohydrate and the dihydrate. Three CGP isomers exist, namely β-glycerophosphoric acid calcium salt $((HOCH_2)_2CHOPO_3Ca$ and D(+)- and L(−)-α-glycerophosphoric acid calcium salt $(HOCH_2CH(OH)CH_2OPO_3Ca)$. Any one isomer, or any combination of two or more isomers may be used as the CGP according to the invention. A commercially available form of CGP is a mixture of calcium β and DL-α-glycerophosphates, and this is a preferred CGP according to the invention. The preferred form of CGP is food grade CGP according *Foods Chemical Codex* (FCC) III, and may be obtained from Gallard Schlesinger Company, Carl Place, N.Y. 11514, which is a distributor for the Dr. Paul Lohmann GmbH KG of Emmerthal, Germany.

CGP is odorless, almost tasteless, and forms a fine, slightly hygroscopic powder. CGP may also be formed into tablets, and may be dissolved into water. The solubility of CGP is about 1 gram in about 50 mL of water. FCC III lists CGP as a nutrient/dietary supplement, but does not indicate that CGP is either an alkali or a buffer/neutralizing agent.

Where CGP is formulated into a composition for dermatological application to the skin, the composition may generally contain from about 1 wt % up to about 100 wt % CGP, preferably about 10 wt % to about 95 wt % CGP, and more preferably about 25 wt % to about 75 wt % CGP. Those skilled in the art will understand that the concentration of CGP can be adjusted to the particular condition being treated and/or the particular vehicle being used and may be limited by such factors as solubility in or compatibility with the particular vehicle or other formulation ingredients selected.

Compositions containing CGP may be applied contemporaneously with other topical agents to provide synergistic or amplified activity to treat a particular dermatological condition. Examples of various preferred combinations include the following. For deodorant use, for example, CGP may be combined with other agents typically used for this purpose, including but not limited to aluminum salts, zirconium salts, zinc salts, and bicarbonate salts, such as aluminum chloride, aluminum chlorhydroxide, aluminum sulfate, aluminum potassium sulfate, aluminum phenolsulfonate, zirconium oxychloride, zirconium hydroxychloride, zinc oxide, zinc peroxide, zinc stearate, zinc phenolsulfonate, sodium bicarbonate, or mixtures thereof. For use in treating dermatological discomfort, CGP may be combined with, for example, resorcinol, zinc oxide, lanolin, petrolatum, hydrocortisone, aloe vera extract, and talc.

CGP may be applied to treat dermatological conditions in various physical formulations including, but not limited to, solutions, gels, creams, lotions, stick, balm, sprays or powders in either anhydrous or aqueous vehicles. CGP may also be formulated with a variety of vehicles or carrier agents. For example, CGP can be used as a pure powder in a very fine grind or mixed with carriers such as cornstarch, talc, and other powders. CGP can also be dissolved and used in either an aqueous or non-aqueous (oil) liquid medium. CGP can also be dissolved or used as a suspended solid in a salve, ointment, or cream, with or without other additives such as perfumes or surfactants.

The invention will now be described in more detail with reference to the following specific, non-limiting example.

EXAMPLE 1

Use of calcium glycerophosphate for control of underarm odor and wetness.

A composition of CGP with cornstarch as a carrier in a 1:3 ratio, i.e., 25 weight percent CGP, was demonstrated by an informal test panel as an effective composition for underarm wetness and odor control. Twelve subjects compared the effectiveness of CGP in controlling odor and wetness by applying the CGP/cornstarch composition under their left arm and their regular deodorant/antiperspirant under their right arm, with the sequence being reversed daily for five days. The results shown below in Table I demonstrate that the CGP/composition was effective in odor and wetness control. Nine out of twelve test subjects rated the CGP composition equal to or better than their regular antiperspirant/deodorant on wetness control. Five out of twelve test subjects rated the CGP composition equal to or better than their regular antiperspirant/deodorant on odor control. In this regard, it should be noted that no perfuming or odor-covering agent was employed. Finally, ten out of twelve test subjects rated the CGP composition equal to or better than their regular antiperspirant/deodorant with regard to a feeling of comfort.

TABLE I

Comparison of CGP/cornstarch composition with commercial antiperspirant/deodorant products for odor and wetness control.

|  | commercial product preferred[1] | CGP-formulation preferred[2] | no preference |
| --- | --- | --- | --- |
| wetness control | 3 | 7 | 2 |
| odor control | 7 | 4 | 1 |
| comfort | 2 | 6 | 4 |

[1]Test subjects compared a CGP formulation with their own particular commercially available brand of deodorant/antiperspirant.
[2]The CGP formulation consisted of approximately 25 wt % CGP and 75 wt % cornstarch.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of treating dermal body odor in humans comprising topically applying calcium glycerophosphate to an area of skin affected by body odor.

2. The method according to claim 1, wherein the body odor affected area is selected from the group consisting of an underarm area, a foot area, a facial area, scalp area, and an anal-genital area.

3. The method according to claim 1, wherein the calcium glycerophosphate is applied in a form selected from the group consisting of liquid spray, powder, roll-on, solid stick applicator, and semi-solid vehicle.

4. The method according to claim 1, wherein the calcium glycerophosphate is applied in a vehicle selected from the group consisting of aqueous liquid, non-aqueous liquid, salve, ointment, cream, and powdered solid excipient.

5. The method according to claim 1, wherein the calcium glycerophosphate is present in a formulation which further comprises an active ingredient selected from the group consisting of aluminum salts, zirconium salts and zinc salts.

* * * * *